US006949655B2

United States Patent
Lauffer et al.

(10) Patent No.: US 6,949,655 B2
(45) Date of Patent: Sep. 27, 2005

(54) ACYCLIC PIPERIDINE DERIVATIVES

(76) Inventors: David Lauffer, 254 Taylor Rd., Stow, MA (US) 01775; Ronald Tomlinson, 317 Dicenzo Blvd., Marlborough, MA (US) 07152; Eckhard Ottow, Moltkestrasse 48, 12203 Berlin (DE); Martyn Botfield, 363 Marlborough St., #6, Boston, MA (US) 02115

( * ) Notice: Subject to any disclaimer, the term of this patent is extended or adjusted under 35 U.S.C. 154(b) by 0 days.

(21) Appl. No.: 10/170,965

(22) Filed: Jun. 13, 2002

(65) Prior Publication Data

US 2003/0191117 A1 Oct. 9, 2003

Related U.S. Application Data

(60) Provisional application No. 60/298,328, filed on Jun. 14, 2001.

(51) Int. Cl.$^7$ .............................................. C07D 211/16
(52) U.S. Cl. ..................... 546/255; 546/262; 546/314; 546/328
(58) Field of Search ................................ 546/255, 262, 546/314, 328; 514/315, 316, 326

(56) References Cited

U.S. PATENT DOCUMENTS 2,957,881 A    10/1960  Hoffmann et al. .......... 546/189

FOREIGN PATENT DOCUMENTS

WO    WO 99/55688    11/1999

OTHER PUBLICATIONS

Oda, Ryohei; Katsuragawa, Seiichi; Ito, Yoshihiko; Okano, Masaya, Nippon Kagaku Zasshi, 87(11), 1236–8 (Japanese) 1966, Chemical Abstracts 66:94892.*

Shanker, et al., Database Crossfire Beilstein, Beilstein Institut zur Förderung der Chemischen Wissenschaften, Frankfurt am Main, DE; database accession No. brn 543330, brn 53519, J. Prakt. Chem., 30:10 (1965).

* cited by examiner

Primary Examiner—Thomas C. McKenzie
(74) Attorney, Agent, or Firm—Nandakumar Govindaswamy; Vertex Pharmaceuticals Incorporated

(57) ABSTRACT

A compound having the formula (I):

wherein:

each $R^1$, $R^2$, $R^3$ and $R^4$ are independently selected from ($C_1$–$C_{10}$)-straight or branched alkyl, Ar-substituted-($C_1$–$C_{10}$)-straight or branched alkyl, ($C_2$–$C_{10}$)-straight or branched alkenyl or alkynyl, or Ar-substituted-($C_2$–$C_{10}$)-straight or branched alkenyl or alkynyl; wherein one to two $CH_2$ groups of said alkyl, alkenyl, or alkynyl chains in each of $R^1$, $R^2$, $R^3$ and $R^4$ are optionally and independently replaced with O, S, S(O), S(O), $S(O)_2$, C(O) or $N(R^5)$ in a chemically stable arrangement, wherein the $CH_2$ group of $R^1$ and $R^2$ bound directly to said nitrogen cannot be replaced with C(O); or $R^1$ and $R^2$ taken together form a 4 to 7 membered ring; or $R^3$ and $R^4$ taken together form a 3 to 7 membered ring; wherein a $CH_2$ in either the $R^1$ and $R^2$ ring system or the $R^3$ and $R^4$ ring system is independently and optionally replaced with O, C(O), $N(R^5)$, S, S(O), S(O)2 in a chemically stable arrangement; or wherein either or both of the $R^1$ and $R^2$ ring system and the $R^3$ and $R^4$ ring system is optionally fused with Ar.

These compounds are useful for treating or preventing neuronal damage, particularly damage associated with neurological diseases. These compounds are also useful for stimulating nerve growth. The invention also provides compositions comprising these compounds, and methods of utilizing those compositions for treating or preventing neuronal damage or for stimulating nerve growth.

7 Claims, No Drawings

ACYCLIC PIPERIDINE DERIVATIVES

CROSS-REFERENCE TO RELATED APPLICATIONS

This application claims the benefit of U.S. Provisional application No. 60/298,328, filed Jun. 14, 2001.

TECHNICAL FIELD OF THE INVENTION

The present invention relates to acyclic piperazine and piperidine derivatives, which are especially useful for treating or preventing neuronal damage, particularly damage associated with neurological diseases. These compounds are also useful for stimulating nerve growth. The invention also provides compositions comprising the compounds of the present invention and methods of utilizing those compositions for treating or preventing neuronal damage or for stimulating nerve growth.

BACKGROUND OF THE INVENTION

Neurological diseases are associated with the death of or injury to neuronal cells. Typical treatment of neurological diseases involves drugs capable of inhibiting neuronal cell death. A more recent approach involves the promotion of nerve regeneration by promoting neuronal growth.

Neuronal growth, which is critical for the survival of neurons, is stimulated in vitro by nerve growth factors (NGF). For example, Glial Cell Line-Derived Neurotrophic Factor (GDNF) demonstrates neurotrophic activity both, in vivo and in vitro, and is currently being investigated for the treatment of Parkinson's disease. Insulin and insulin-like growth factors have been shown to stimulate growth of neurites in rat pheochromocytoma PC12 cells and in cultured sympathetic and sensory neurons [Recio-Pinto et al., *J. Neurosci.*, 6, pp. 1211–1219 (1986)]. Insulin and insulin-like growth factors also stimulate the regeneration of injured motor nerves in vivo and in vitro [Near et al., *Proc. Natl. Acad. Sci.*, pp. 89, 11716–11720 (1992); and Edbladh et al., *Brain Res.*, 641, pp. 76–82 (1994)]. Similarly, fibroblast growth factor (FGF) stimulates neural proliferation [D. Gospodarowicz et al., *Cell Differ.*, 19, p. 1 (1986)] and growth [M. A. Walter et al., *Lymphokine Cytokine Res.*, 12, p. 135 (1993)].

There are, however, several disadvantages associated with the use of nerve growth factors for treating neurological diseases. They do not readily cross the blood-brain barrier. They are unstable in plasma and they have poor drug delivery properties.

Recently, small molecules have been shown to stimulate neurite outgrowth in vivo. In individuals suffering from a neurological disease, this stimulation of neuronal growth protects neurons from further degeneration, and accelerates the regeneration of nerve cells. For example, estrogen has been shown to promote the growth of axons and dendrites, which are neurites sent out by nerve cells to communicate with each other in a developing or injured adult brain [(C. Dominique Toran-Allerand et al., *J. Steroid Biochem. Mol. Biol.*, 56, pp. 169–78 (1996); and B. S. McEwen et al., *Brain Res. Dev. Brain. Res.*, 87, pp. 91–95 (1995)]. The progress of Alzheimer's disease is slowed in women who take estrogen. Estrogen is hypothesized to complement NGF and other neurotrophins and thereby help neurons differentiate and survive.

Other target sites for the treatment of neurodegenerative disease are the immunophilin class of proteins. Immunophilins are a family of soluble proteins that mediate the actions of immunosuppressant drugs such as cyclosporin A, FK506 and rapamycin. Of particular interest is the 12 kDa immunophilin, FK-506 binding protein (FKBP12). FKBP12 binds FK-506 and rapamycin, leading to an inhibition of T-cell activation and proliferation. Interestingly, the mechanism of action of FK-506 and rapamycin are different. For a review, see, S. H. Solomon et al., *Nature Med.*, 1, pp. 32–37 (1995). It has been reported that compounds with an affinity for FKBP12 that inhibit that protein's rotomase activity possess nerve growth stimulatory activity. [Lyons et al., *Proc. Natl. Acad. Sci. USA*, 91, pp. 3191–3195 (1994)]. Many of these such compounds also have immunosuppressive activity.

FK506 (Tacrolimus) has been demonstrated to act synergistically with NGF in stimulating neurite outgrowth in PC12 cells as well as sensory ganglia [Lyons et al. (1994)]. This compound has also been shown to be neuroprotective in focal cerebral ischemia [J. Sharkey and S. P. Butcher, *Nature*, 371, pp. 336–339 (1994)] and to increase the rate of axonal regeneration in injured sciatic nerve [B. Gold et al., *J. Neurosci.*, 15, pp. 7509–16 (1995)].

The use of immunosuppressive compounds, however, has drawbacks in that prolonged treatment with these compounds can cause nephrotoxicity [Kopp et al., *J. Am. Soc. Nephrol.*, 1, p. 162 (1991)], neurological deficits [P. C. DeGroen et al., *N. Eng. J. Med.*, 317, p. 861 (1987)] and vascular hypertension [Kahan et al., *N. Eng. J. Med.*, 321, p. 1725 (1989)].

Sub-classes of FKBP binding compounds which inhibit rotomase activity, but which purportedly lack immunosuppressive function have been disclosed for use in stimulating nerve growth and for neuroprotection [see, U.S. Pat. No. 5,614,547; WO 96/40633; WO 96/40140; WO 97/16190; WO 98/13343; WO 98/13355; WO 98/29116; WO 98/29117; WO 98/35675; WO 98/37882; WO 98/37885; J. P. Steiner et al., *Proc. Natl. Acad. Sci. USA*, 94, pp. 2019–23 (1997); and G. S. Hamilton et al., *Bioorg. Med. Chem. Lett.*, 7, pp. 1785–90 (1997)].

Stimulation of neural axons in nerve cells by piperidine derivatives is described in WO 96/41609. Clinical use of the piperidine and pyrrolidine derivatives known so far for stimulating axonal growth has not been promising, as the compounds are unstable in plasma and do not pass the blood-brain barrier in adequate amounts.

More recently, classes of compounds which lack the ability to bind FKBP and lack immunosuppressive function have been described for use in stimulating nerve growth and preventing neurodegeneration [see, WO 98/20891; WO 98/20892; WO 98/20893 and WO 99/10340]

Though a wide variety of compounds for treating or preventing neurological degenerative diseases have been described, only two of these are currently in clinical trials and none have been approved for commercialization. And while compounds which share certain structural similarities to the compounds disclosed herein have been described in U.S. Pat. Nos. 4,115,569 and 4,374,990, neither of those patents specifically teach or suggest the compounds of the present invention, nor is there any teaching that such compounds would have utility in stimulating nerve growth or preventing neurodegeneration.

Thus, there remains a need for the discovery and design of new compounds and compositions that have the ability to prevent and/or treat neuronal damage associated with neuropathologic conditions.

SUMMARY OF THE INVENTION

The present invention provides compounds having formula (I):

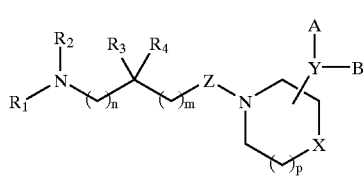

wherein:
  each $R^1$, $R^2$, $R^3$ and $R^4$ are independently selected from $(C_1-C_{10})$-straight or branched alkyl, Ar-substituted-$(C_1-C_{10})$-straight or branched alkyl, $(C_2-C_{10})$-straight or branched alkenyl or alkynyl, or Ar-substituted-$(C_2-C_{10})$-straight or branched alkenyl or alkynyl; wherein
    one to two $CH_2$ groups of said alkyl, alkenyl, or alkynyl chains in each of $R^1$, $R^2$, $R^3$ and $R^4$ are optionally and independently replaced with O, S, S(O), $S(O)_2$, C(O) or $N(R^5)$ in a chemically stable arrangement, wherein the $CH_2$ group of $R^1$ and $R^2$ bound directly to said nitrogen cannot be replaced with C(O); or
  $R^1$ and $R^2$ taken together form a 4 to 7 membered ring; or
  $R^3$ and $R^4$ taken together form a 3 to 7 membered ring; wherein a $CH_2$ in either the $R^1$ and $R^2$ ring system or the $R^3$ and $R^4$ ring system is independently and optionally replaced with O, C(O), $N(R^5)$, S, S(O), S(O)2 in a chemically stable arrangement; or
  wherein either or both of the $R^1$ and $R^2$ ring system and the $R^3$ and $R^4$ ring system is independently and optionally fused with a phenyl ring;
    wherein said phenyl ring is optionally and independently substituted with one to three substituents selected from halo, hydroxy, nitro, =O, —$SO_3H$, trifluoromethyl, trifluoromethoxy, $(C_1-C_6)$-straight or branched alkyl, $(C_1-C_6)$-straight or branched alkenyl, O-[$(C_1-C_6)$-straight or branched alkyl], O—[$(C_1-C_6)$-straight or branched alkenyl], O-benzyl, O-phenyl, 1,2-methylenedioxy, $\geq N(R^6)(R^7)$, carboxyl, N-($C_1-C_6$-straight or branched alkyl or $C_2-C_6$-straight or branched alkenyl) carboxamides, N,N-di-($C_1-C_6$-straight or branched alkyl or $C_2-C_6$-straight or branched alkenyl) carboxamides, N-($C_1-C_6$-straight or branched alkyl or $C_2-C_6$-straight or branched alkenyl) sulfonamides, or N,N-di-($C_1-C_6$-straight or branched alkyl or C2–C6-straight or branched alkenyl) sulfonamides;
  Ar is selected from phenyl, 1-naphthyl, 2-naphthyl, indenyl, azulenyl, 2-furyl, 3-furyl, 2-thienyl, 3-thienyl, 2-pyridyl, 3-pyridyl, 4-pyridyl, pyrrolyl, oxazolyl, thiazolyl, imidazolyl, pyraxolyl, pyrazolinyl, pyraolidinyl, isoxazolyl, isothiazolyl, 1,2,3-oxadiazolyl, 1,2,3-triazolyl, 1,3,4-thiadiazolyl, 1,2,4-triazolyl, 1,2,4-oxadiazolyl, 1,2,4-thiadiazolyl, 1,2,3-thiadiazolyl, benoxazolyl, pyridazinyl, 2-pyrimidinyl, 4-pyrimidinyl, 5-pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, 1,2,3,4-tetrahydroisoquinolinyl, isoquinolinyl, 1,2,3,4-tetrahydroquinolinyl, cinnolinyl, phthalazinyl, quinazolinyl, quinoxalinyl, 1,8-naphthyridinyl, or any other chemically stable monocyclic or bicyclic ring system, wherein each ring consists of 5 to 7 ring atoms and wherein each ring comprises 0 to 3 heteroatoms independently selected from N, O, or S in a chemically stable arrangement, wherein each Ar is optionally and independently substituted with one to three substituents selected from halo, hydroxy, nitro, —O, —$SO_3H$, trifluoromethyl, trifluoromethoxy, $(C_1-C_6)$-straight or branched alkyl, $(C_1-C_6)$-straight or branched alkenyl, O—[$(C_1-C_6)$-straight or branched alkyl], O—[$(C_1-C_6)$-straight or branched alkenyl], O-benzyl, O-phenyl, 1,2-methylenedioxy, —$N(R^6)$($R^7$), carboxyl, N-($C_1-C_6$-straight or branched alkyl or $C_2-C_6$-straight or branched alkenyl) carboxamides, N,N-di-($C_1-C_6$-straight or branched alkyl or $C_2-C_6$-straight or branched alkenyl) carboxamides, N-($C_1-C_6$-straight or branched alkyl or $C_2-C_6$-straight or branched alkenyl) sulfonamides, or N,N-di-($C_1-C_6$-straight or branched alkyl or C2–C6-straight or branched alkenyl) sulfonamides;

each of $R^6$ and $R^7$ are independently selected from $(C_1-C_6)$-straight or branched alkyl, $(C_2-C_6)$-straight or branched alkenyl or alkynyl, hydrogen, phenyl or benzyl; or wherein $R^6$ and $R^7$ are taken together with the nitrogen atom to which they are bound to form a 5–7 membered heterocyclic ring;

each $R^5$ is independently selected from hydrogen, $(C_1-C_6)$-straight or branched alkyl, or $(C_2-C_6)$-straight or branched alkenyl or alkynyl;

n is 0 or 1 and m is 0 or 1;

X is selected from $C(R^5)_2$, $N(R^5)$, N, O, S, S(O), or $S(O)_2$

Y is selected from a bond, $(C_1-C_6)$-straight or branched) alkyl, or $(C_2-C_6)$-straight or branched) alkenyl or alkynyl; wherein one to two of the $CH_2$ groups of said alkyl, alkenyl, or alkynyl is optionally and independently replaced with O, S, S(O), $S(O)_2$, C(O) or $N(R^5)$ in a chemically stable arrangement;

Z is —C(O)— or —$CH_2$— p is 0, 1 or 2;

each of A and B is independently selected from hydrogen or Ar; or one of A or B is absent; and wherein two carbon ring atoms in the depicted ring structure containing X and N are optionally linked to one another via a $C_1-C_4$ straight alkyl or a $C_2-C_4$ straight alkenyl to create a bicyclic moiety.

In another embodiment, the invention provides pharmaceutical compositions comprising the compounds of formula (I). These compositions may be utilized in methods for promoting neuronal repair or preventing neuronal damage in a patient or in an ex vivo nerve cell. More particularly, the methods of this invention are useful in treating various neurological diseases. Examples of such diseases include peripheral nerve destruction due to physical injury or diseases such as diabetes; physical injuries to the central nervous system (e.g., brain or spinal cord); stroke; neurological disturbances due to nerve degeneration, such as Parkinson's disease, Alzheimer's disease, and amylotrophic lateral sclerosis.

DETAILED DESCRIPTION OF THE INVENTION

The present invention provides compounds having formula (I):

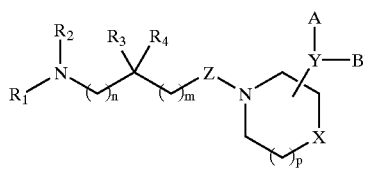

(I)

wherein:

each $R^1$, $R^2$, $R^3$ and $R^4$ are independently selected from t($C_1$–$C_{10}$)-straight or branched alkyl, Ar-substituted-($C_1$–$C_{10}$)-straight or branched alkyl, ($C_2$–$C_{10}$)-straight or branched alkenyl or alkynyl, or Ar-substituted-($C_2$–$C_{10}$)-straight or branched alkenyl or alkynyl; wherein one to two $CH_2$ groups of said alkyl, alkenyl, or alkynyl chains in each of $R^1$, $R^2$, $R^3$ and $R^4$ are optionally and independently replaced with O, S, S(O), S(O)$_2$, C(O) or N($R^5$) in a chemically stable arrangement, wherein the $CH_2$ group of $R^1$ and $R^2$ bound directly to said nitrogen cannot be replaced with C(O); or $R^1$ and $R^2$ taken together form a 4 to 7 membered ring; or $R^3$ and $R^4$ taken together form a 3 to 7 membered ring;

wherein a $CH_2$ in either the $R^1$ and $R^2$ ring system or the $R^3$ and $R^4$ ring system is independently and optionally replaced with O, C(O), N($R^5$), S, S(O), S(O)2 in a chemically stable arrangement; or wherein either or both of the $R^1$ and $R^2$ ring system and the $R^3$ and $R^4$ ring system is independently and optionally fused with a phenyl ring;

wherein said phenyl ring is optionally and independently substituted with one to three substituents selected from halo, hydroxy, nitro, =O, —SO$_3$H, trifluoromethyl, trifluoromethoxy, ($C_1$–$C_6$)-straight or branched alkyl, ($C_1$–$C_6$)-straight or branched alkenyl, O—[($C_1$–$C_6$)-straight or branched alkyl], O—[($C_1$–$C_6$)-straight or branched alkenyl], O-benzyl, O-phenyl, 1,2-methylenedioxy, —N($R^6$)($R^7$), carboxyl, N-($C_1$–$C_6$-straight or branched alkyl or $C_2$–$C_6$-straight or branched alkenyl) carboxamides, N,N-di-($C_1$–$C_6$-straight or branched alkyl or $C_2$–$C_6$-straight or branched alkenyl) carboxamides, N-($C_1$–$C_6$-straight or branched alkyl or $C_2$–$C_6$-straight or branched alkenyl) sulfonamides, or N,N-di-($C_1$–$C_6$-straight or branched alkyl or C2–C6-straight or branched alkenyl) sulfonamides;

Ar is selected from phenyl, 1-naphthyl, 2-naphthyl, indenyl, azulenyl, 2-furyl, 3-furyl, 2-thienyl, 3-thienyl, 2-pyridyl, 3-pyridyl, 4-pyridyl, pyrrolyl, oxazolyl, thiazolyl, imidazolyl, pyraxolyl, pyrazolinyl, pyraolidinyl, isoxazolyl, isothiazolyl, 1,2,3-oxadiazolyl, 1,2,3-triazolyl, 1,3,4-thiadiazolyl, 1,2,4-triazolyl, 1,2,4-oxadiazolyl, 1,2,4-thiadiazolyl, 1,2,3-thiadiazolyl, benoxazolyl, pyridazinyl, 2-pyrimidinyl, 4-pyrimidinyl, 5-pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, 1,2,3,4-tetrahydroisoquinolinyl, isoquinolinyl, 1,2,3,4-tetrahydroquinolinyl, cinnolinyl, phthalazinyl, quinazolinyl, quinoxalinyl, 1,8-naphthyridinyl, or any other chemically stable monocyclic or bicyclic ring system, wherein each ring consists of 5 to 7 ring atoms and wherein each ring comprises 0 to 3 heteroatoms independently selected from N, O, or S in a chemically stable arrangement, wherein each Ar is optionally and independently substituted with one to three substituents selected from halo, hydroxy, nitro, =O, —SO$_3$H, trifluoromethyl, trifluoromethoxy, ($C_1$–$C_6$)-straight or branched alkyl, ($C_1$–$C_6$)-straight or branched alkenyl, O—[($C_1$–$C_6$)-straight or branched alkyl], O—[($C_1$–$C_6$)-straight or branched alkenyl], O-benzyl, O-phenyl, 1,2-methylenedioxy, —N($R^6$)($R^7$), carboxyl, N-($C_1$–$C_6$-straight or branched aklyl or $C_2$–$C_6$-straight or branched alkenyl) carboxamides, N,N-di-($C_1$–$C_6$-straight or branched alkyl or $C_2$–$C_6$-straight or branched alkenyl) carboxamides, N-($C_1$–$C_6$-straight or branched alkyl or $C_2$–$C_6$-straight or branched alkenyl) sulfonamides, or N,N-di-($C_1$–$C_6$-straight or branched alkyl or C2–C6-straight or branched alkenyl) sulfonamides;

each of $R^6$ and $R^7$ are independently selected from ($C_1$–$C_6$)-straight or branched alkyl, ($C_2$–$C_6$)-straight or branched alkenyl or alkynyl, hydrogen, phenyl or benzyl; or wherein $R^6$ and $R^7$ are taken together with the nitrogen atom to which they are bound to form a 5–7 membered heterocyclic ring;

each $R^5$ is independently selected from hydrogen, ($C_1$–$C_6$)-straight or branched alkyl, or ($C_2$–$C_6$)-straight or branched alkenyl or alkynyl;

n is 0 or 1 and m is 0 or 1;

X is selected from C($R^5$)$_2$, N($R^5$), N, O, S, S(O), or S(O)$_2$;

Y is selected from a bond, ($C_1$–$C_6$)-straight or branched) alkyl, or ($C_2$–$C_6$)-straight or branched) alkenyl or alkynyl; wherein one to two of the $CH_2$ groups of said alkyl, alkenyl, or alkynyl is optionally and independently replaced with O, S, S(O), S(O)$_2$, C(O) or N($R^5$) in a chemically stable arrangement;

Z is —C(O)— or —CH$_2$— p is 0, 1 or 2;

each of A and B is independently selected from hydrogen or Ar; or one of A or B is absent; and wherein two carbon ring atoms in the depicted ring structure containing X and N are optionally linked to one another via a $C_1$–$C_4$ straight alkyl or a $C_2$–$C_4$ straight alkenyl to create a bicyclic moiety.

The term "ring atom", as used herein, refers to a backbone atom that makes up the ring. Such ring atoms are selected from C, N, O or S and are bound to 2 or 3 other such ring atoms (3 in the case of certain ring atoms in a bicyclic ring system) in a chemically stable arrangement. The term "ring atom" does not include hydrogen.

The term "chemically stable arrangement", as used herein, refers to a compound structure that renders the compound sufficiently stable to allow manufacture and administration to a mammal by methods known in the art. Typically, such compounds are stable at a temperature of 40° C. or less, in the absence of moisture or other chemically reactive condition, for at least a week.

It will be readily apparent to those of skill in the are that the terms "alkyl" and "alkenyl" when used in the definition of Y represent those portions of an aliphatic moiety for which proper valence is completed by the moities bound to Y (i.e., at one end, the ring atom to which Y is bound; and at the other end, A and B). Thus, as an example, for the purposes of this invention, Y is considered a $C_2$ alkyl in each of the following structures (the moiety representing Y being shown in bold):

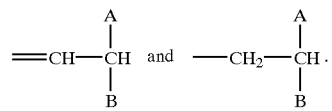

According to one preferred embodiment, Z is —C(O)—.

According to another preferred embodiment, each of $R^1$ and $R^2$ is independently selected from $(C_1-C_6)$-straight alkyl, or $(C_1-C_6)$-straight alkyl-Ar. Even more preferred is when $R^1$ and/or $R^2$ is selected from methyl, ethyl, benzyl, chlorobenzyl, dichlorobenzyl, bromobenzyl, fluorobenzyl or methoxybenzyl. Most preferred is when $R^1$ and/or $R^2$ is selected from methyl, ethyl, 3-methyl-but-2-enyl, benzyl, 3-methoxy benzyl, or 3-fluoro benzyl.

In yet another preferred embodiment, p is 0 or 1; and X is C or N. More preferably p is 1.

In another preferred embodiment of the compound of formula (I), Y is a bond, —O— or —CH.

According to another preferred embodiment, one of A or B is selected from phenyl or pyridyl and the other of A or B is selected from hydrogen, phenyl or pyridyl. Even more preferred is when one of A or B is selected from phenyl, fluorophenyl, chlorophenyl or dichlorophenyl and the other is selected from phenyl, fluorophenyl, hydrogen or is absent.

Some of the more preferred embodiments of this invention are the compounds listed in Table 1, below and the compounds set forth in the Examples.

TABLE 1

| # | Structure |
|---|---|
| 1 | 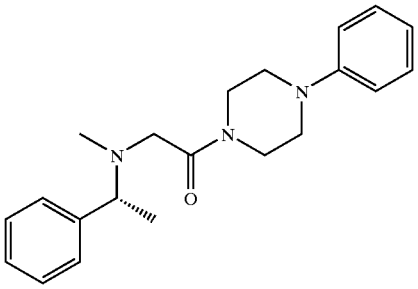 |
| 2 | 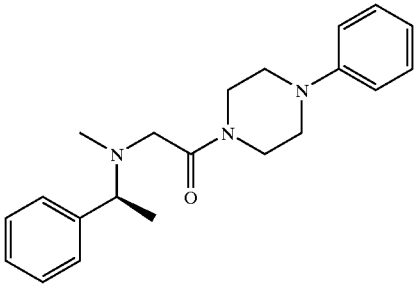 |

TABLE 1-continued

| # | Structure |
|---|---|
| 3 | 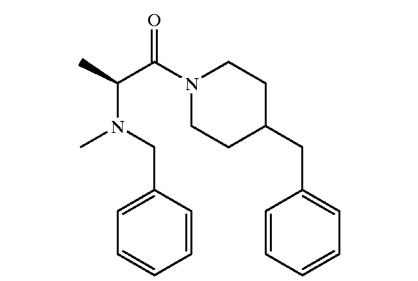 |
| 4 | 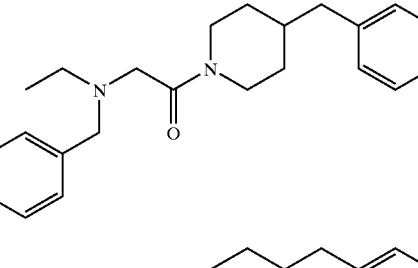 |
| 5 | 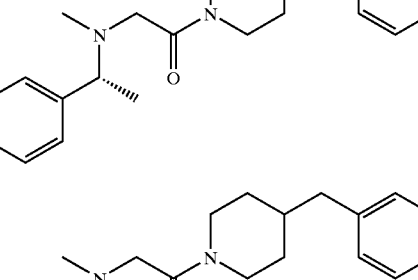 |
| 6 | 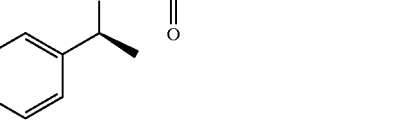 |
| 7 | 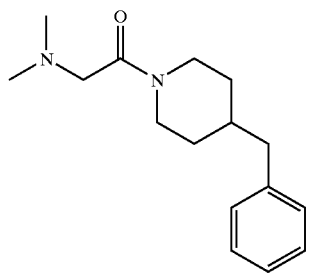 |
| 8 | 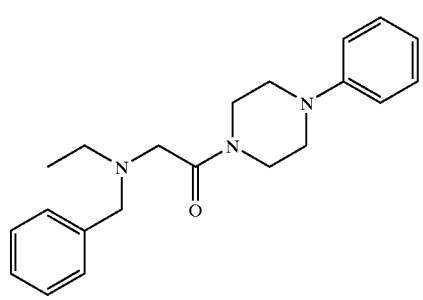 |

TABLE 1-continued

| # | Structure |
|---|-----------|
| 9 | 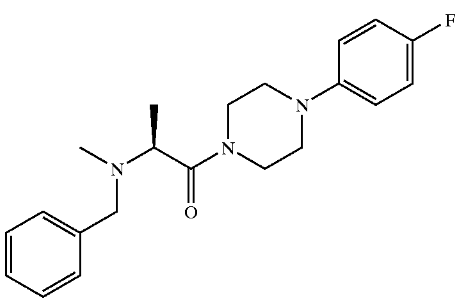 |
| 10 | 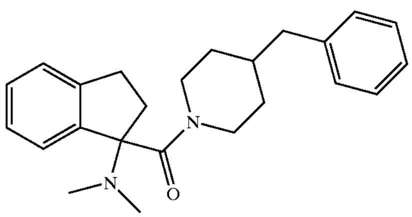 |
| 11 | 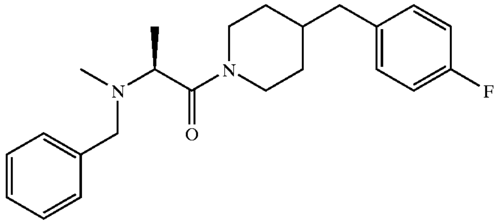 |
| 12 | 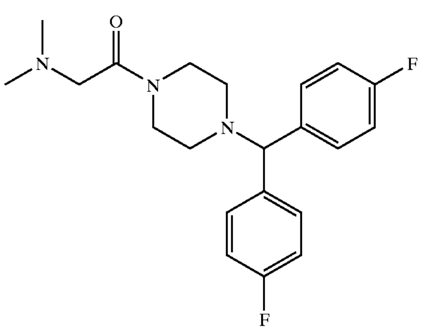 |
| 13 | 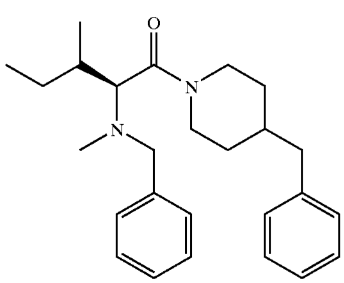 |
| 14 | |
| 15 | |
| 16 | |
| 17 | |

TABLE 1-continued

| # | Structure |
|---|---|
| 18 | 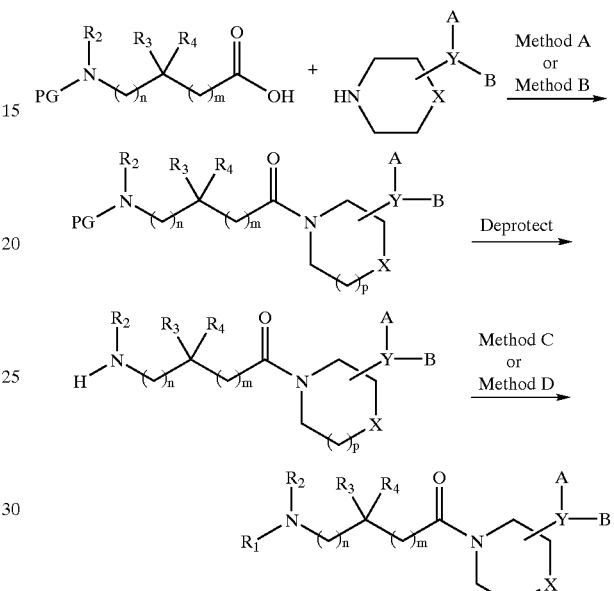 |
| 19 | 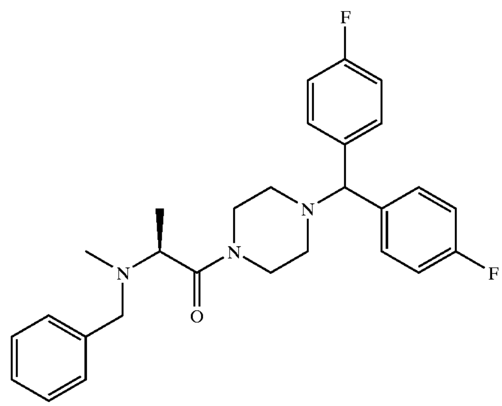 |
| 20 | 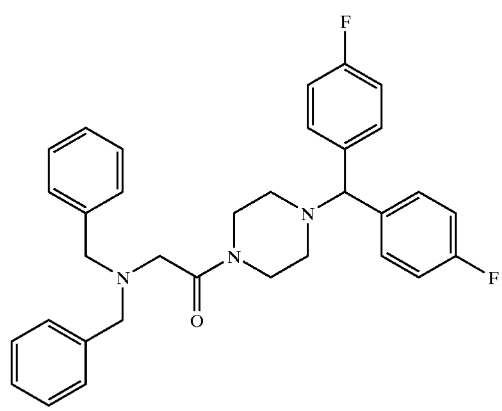 |
| 21 | 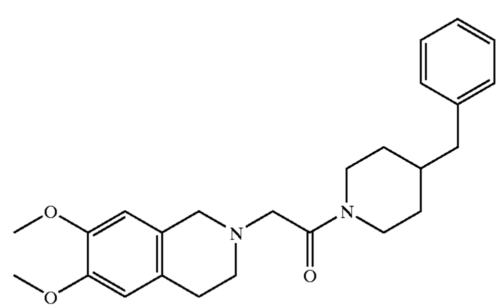 |

The compounds of formula (I) may be stereoisomers, geometric isomers or stable tautomers. The invention envisions all possible isomers, such as E and Z isomers, S and R enantiomers, diastereoisomers, racemates, and mixtures of those.

The compounds of the present invention may be readily prepared using known synthetic methods. For example, compounds of formula (I) may be prepared as shown below in any of Schemes 1 through 4:

SCHEME 1

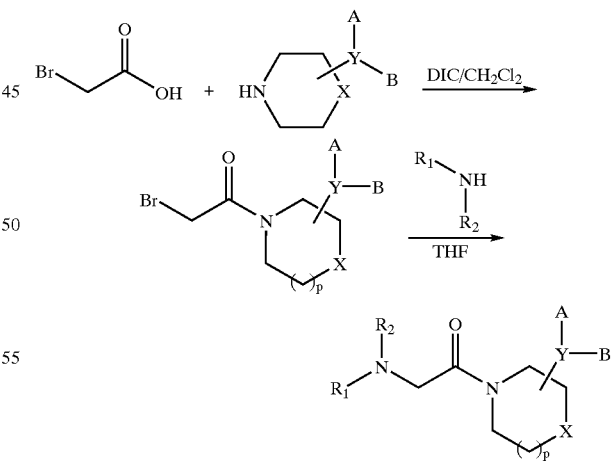

Method A: pivaloyl chloride, diisopropylethylamine, CH$_2$Cl$_2$
Method B: HOBT, EDC (or other amide coupling reagents), CH$_2$Cl$_2$
Method C: R$_1$CH$_2$—Br, K$_2$CO$_3$, CH$_3$CN or DMF
Method D: R$_1$CH$_2$—Br, Et$_3$N, Bu$_4$NI (cat.), CH$_2$Cl$_2$

SCHEME 2

SCHEME 3

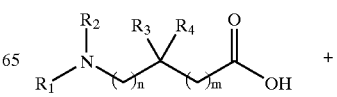

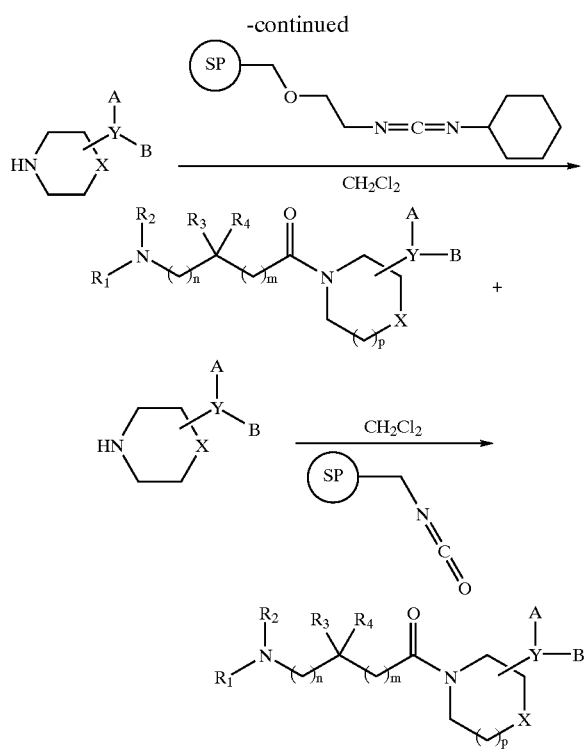

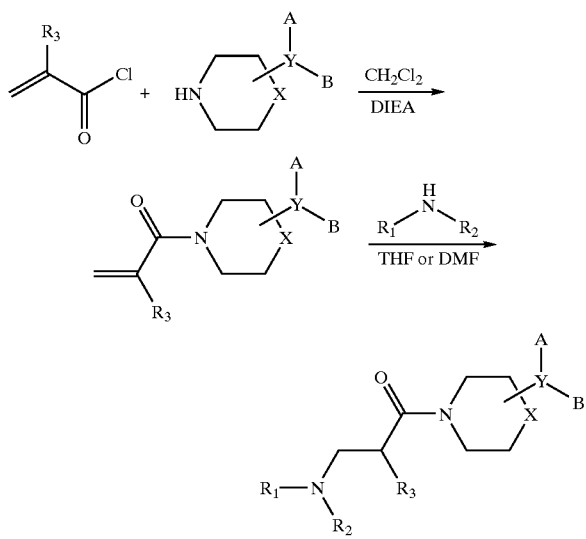

SCHEME 4

In the schemes depicted above, the following abbreviations are used: Et$_3$N=triethyl-amine; DIEA=diisopropylethylamine; CH$_2$Cl$_2$=dichloromethane DMF=dimethylformamide; THF=tetrahydrofuran; Bu4NI=tetrabutylammonium iodide; HOBT=N-hydroxybenzotriazole; EDC=1-(3-Dimethyl-aminopropyl)-3-ethylcarbodiimide hydrochloride. Schemes 3 is combinatorial chemistry type wherein reactants linked to a polystyrene solid support ("SP") are used.

Each of these schemes are described in more detail in the Example section.

One of skill in the art will be well aware of analogous synthetic methods for preparing compounds of formula (I).

The nerve growth stimulatory activity of the compounds of this invention may be initially assayed using several cell culture assays known in the art. For example, the compounds of this invention may be tested in a neurite outgrowth assay using pheochromocytoma PC12 cells as described by Lyons et al., *PNAS*, 91, pp. 3191–3195 (1994). A similar assay may be carried out in SH-SY5Y human neuroblastoma cells. Alternatively, the chick dorsal root ganglia assay described in U.S. Pat. No. 5,614,547 or in G. S. Hamilton et al., *Bioorg. Med. Chem. Lett.*, (1997) and references cited therein, may be utilized.

The compounds of this invention may also be assayed for nerve growth stimulatory activity in vivo using a mouse model of Parkinson's disease [J. P. Steiner et al., *Proc. Natl. Acad. Sci. USA*, 94, pp. 2019–23 (1997), U.S. Pat. No. 5,721,256] or following surgical sciatic nerve crush in rats.

The neuroprotective activity of the compounds of this invention may be assayed using rat embryo ventral mesencephalic cells in culture which are subsequently exposed to the glutamate receptor agonist NMDA. This assay is described in detail in the example section.

According to another embodiment, this invention provides compositions comprising a compound of formula (I) and a pharmaceutically acceptable carrier.

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxy methylcellulose, polyacrylates, waxes, polyethylene-polyoxypropylene-block polymers, polyethylene glycol and wool fat.

In another embodiment, the pharmaceutical composition of the present invention is comprised of a compound of formula (I), a pharmaceutically acceptable carrier, and a neurotrophic factor.

The term "neurotrophic factor," as used herein, refers to compounds which are capable of stimulating growth or proliferation of nervous tissue. Numerous neurotrophic factors have been identified in the art and any of those factors may be utilized in the compositions of this invention. These neurotrophic factors include, but are not limited to, nerve growth factor (NGF), insulin-like growth factor (IGF-1) and its active truncated derivatives such as gIGF-1 and Des(1–3) IGF-I, acidic and basic fibroblast growth factor (aFGF and bFGF, respectively), platelet-derived growth factors (PDGF), brain-derived neurotrophic factor (BDNF), ciliary neurotrophic factors (CNTF), glial cell line-derived neurotrophic factor (GDNF), neurotrophin-3 (NT-3)and neurotrophin 4/5 (NT-4/5). The most preferred neurotrophic factor in the compositions of this invention is NGF.

As used herein, the described compounds used in the pharmaceutical compositions and methods of this invention, are defined to include pharmaceutically acceptable derivatives thereof. A "pharmaceutically acceptable derivative" denotes any pharmaceutically acceptable salt, ester, or salt of such ester, of a compound of this invention or any other compound which, upon administration to a patient, is capable of providing (directly or indirectly) a compound of this invention, or a metabolite or residue thereof, characterized by the ability to promote repair or prevent damage of neurons from disease or physical trauma.

If pharmaceutically acceptable salts of the described compounds are used, those salts are preferably derived from inorganic or organic acids and bases. Included among such acid salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, 3-phenyl-propionate, picrate, pivalate, propionate, succinate, tartrate, thiocyanate, tosylate and undecanoate. Base salts include ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth. Also, the basic nitrogen-containing groups can be quaternized with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products are thereby obtained.

The described compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of both a described compound and the optional neurotrophic factor that may be combined with the carrier materials to produce a single dosage form will vary depending upon the host treated and the particular mode of administration. Preferably, the compositions should be formulated so that a dosage of between 0.01–100 mg/kg body weight/day of the described compound can be administered. If a neurotrophic factor is present in the composition, then a dosage of between 0.01 µg–100 mg/kg body weight/day of the neurotrophic factor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredients will also depend upon the particular described compound and neurotrophic factor in the composition.

According to another embodiment, this invention provides methods for promoting repair or preventing neuronal damage in vivo or in an ex vivo nerve cell. Such methods comprise the step of treating nerve cells, glial cells, chromafin cells or stem cells with any of the compounds described above. Preferably, this method promotes repair or prevents neuronal damage in a patient, and the compound is formulated into a composition additionally comprising a pharmaceutically acceptable carrier. The amount of the compound utilized in these methods is between about 0.01 and 100 mg/kg body weight/day.

According to an alternate embodiment, the method of promoting repair or preventing neuronal damage comprises the additional step of treating nerve cells with a neurotrophic factor, such as those contained in the pharmaceutical compositions of this invention. This embodiment includes administering the compound and the neurotrophic agent in a single dosage form or in separate, multiple dosage forms. If separate dosage forms are utilized, they may be administered concurrently, consecutively or within less than about 5 hours of one another.

According to another embodiment, the methods of this invention are used to stimulate axonal growth in nerve cells. The compounds are, therefore, suitable for treating or preventing neuronal damage caused by a wide variety of diseases or physical traumas. These include, but are not limited to, Alzheimer's disease, Parkinson's disease, ALS, Huntington's disease, Tourette's syndrome, multiple sclerosis, stroke and ischemia associated with stroke, neural paropathy, other neural degenerative diseases, motor neuron diseases, peripheral neuropathies including chemoneuropathies, sciatic injury, spinal cord or brain injuries, facial nerve damage, nerve damage associated with surgery or chemotherapy, retinopathy, macular degeneration, depression or schizophrenia.

The methods of this invention used to stimulate axonal growth in nerve cells are also useful in increasing nerve graft survival and differentiation, increasing stem cell transplant survival and differentiation, and in increasing glial cell transplant survival and differentiation, In a particularly preferred embodiment of the invention, the method is used to treat a patient suffering from trigeminal neuralgia, glosspharyngeal neuralgia, Bell's Palsy, myasthenia gravis, muscular dystrophy, muscle injury, progressive muscular atrophy, progressive bulbar inherited muscular atrophy, herniated, ruptured, or prolapsed invertebrae disk syndrome's, cervical spondylosis, plexus disorders, thoracic outlet destruction syndromes, peripheral neuropathies, such as those caused by lead, dapsone, ticks, or porphyria, other peripheral myelin disorders, Alzheimer's disease, Gullain-Barre syndrome, Parkinson's disease and other Parkinsonian disorders, ALS, Tourette's syndrome, multiple sclerosis, other central myelin disorders, stroke and ischemia associated with stroke, neural paropathy, other neural degenerative diseases, motor neuron diseases, sciatic injury, neuropathy associated with diabetes, spinal cord injuries, facial nerve injury and other trauma, chemotherapy- and other medication-induced neuropathies, Huntington's disease, and protein fibrillization diseases, such as Diffuse Lewy Body disease, Alzheimer's disease-Lewy Body variant, Famillal British Dementia, and Frontotemporal Dementia.

More preferably, the compositions of the present invention are used for treating Parkinson's disease, amylotrophic lateral sclerosis, Alzheimer's disease, stroke, neuralgias, muscular atrophies, and Guillain-Barré syndrome.

For use of the compounds according to the invention as medications, they are administered in the form of a pharmaceutical preparation containing not only the active ingredient but also carriers, auxiliary substances, and/or additives suitable for enteric or parenteral administration. Administration can be oral or sublingual as a solid in the form of capsules or tablets, as a liquid in the form of solutions, suspensions, elixirs, aerosols or emulsions, or rectal in the form of suppositories, or in the form of solutions for injection which can be given subcutaneously, intramuscularly, or intravenously, or which can be given topically or intrathecally. Auxiliary substances for the desired medicinal formulation include the inert organic and inorganic carriers known to those skilled in the art, such as water, gelatin, gum arabic, lactose, starches, magnesium stearate, talc, vegetable oils, polyalkylene glycols, etc. The medicinal formulations may also contain preservatives, stabilizers, wetting agents, emulsifiers, or salts to change the osmotic pressure or as buffers.

Solutions or suspensions for injection are suitable for parenteral administration, and especially aqueous solutions of the active compounds in polyhydroxy-ethoxylated castor oil.

Surface-active auxiliary substances such as salts of gallic acid, animal or vegetable phospholipids, or mixtures of them, and liposomes or their components, can be used as carrier systems.

The neurotrophic effect of the compounds of formula (I) of the present invention and their physiologically acceptable salts can be determined by the methods of W. E. Lyons et al., *Proc. Natl. Acad. Sci. USA*, Vol. 91, pp. 3191–3195 (1994) and W. E. Lyons et al., *Proc. Natl. Acad. Sci. USA*, Vol. 91, pages 3191–3195 (1994), the disclosures of which are herein incorporated by reference.

In order that this invention be more fully understood, the following examples are set forth. These examples are for the purpose of illustration only and are not to be construed as limiting the scope of the invention in any way.

EXAMPLE 1

Combinatorial Synthesis of Compounds Via Scheme

To N-ethylpipecolinic acid (0.157 g, 1.0 mmol) in 14 mL of dry $CH_2Cl_2$ was added pivaloyl chloride (0.121 g, 1.01 mmol) neat. After 1 hr, 1 mL of the resulting reaction solution was added to 14 wells of a reaction block containing morpholinomethyl polystyrene HL resin (100 mg, 0.4 mmol) and the appropriate amine derivative (0.2 mmol) in 2 mL of dry $CH_2Cl_2$. After shaking for 12 hrs, polystyrene methyl isocyanate (80 mg, 0.1 mmol) was added and the reaction solution was shaken an additional 12 hrs. Filtration and evaporation afforded the crude amide derivatives. Purification was accomplished with solid phase extraction (SPE-C) with methanol and methanol/ammonia to give the desired product. Compounds 1 and 2 were synthesized in this manner.

EXAMPLE 2

Combinatorial Synthesis of Compounds Via Scheme 3

To N-cycloheanecarbodiimide-N'-propyloxymethyl polystyrene resin (150 mg, 0.15 mmol) in the wells of a reaction block was added the appropriate amino acid derivative (0.075 mmol) neat. To each well was added 3 ml of the appropriate amine (0.1 mmol) in dry $CH_2Cl_2$. After shaking for 12 hrs, polystyrene methyl isocyanate (80 mg, 0.05 mmol) was added and the reaction solution was shaken an additional 12 hrs. Filtration and evaporation afforded the crude amide derivatives. Purification was accomplished with reverse phase HPLC with H2O/acetonitrile (0.1% TFA) to give the desired product as a trifluoroacetate salt. Compounds 1, 5, 9, 10, 12, 13 and 19 of Table 2 were prepared by this method.

Combinatorial Synthesis of Compounds Via Scheme 2

2-bromo-1-(4-phenyl-piperazime-1-yl) ethanone (22)

To bromoacetic acid (935 mg, 6.78 mmol) in 30 mL of $CH_2Cl_2$ was added diisopropylcarbodiimide (856 mg, 6.78 mmol). After 0.5 h, the resulting white percipitate was removed by filtration and the filtrate was treated with 1-N-phenylpiperazine (1.10 g, 6.78 mmol) and the solution was stirred for 10 h. Concentration and purification by flash chromatography ($CH_2Cl_2$/EtOAc) afforded the title compound 1.63 g, (84% yield). MS (MH$^+$) m/z 284.91

1-(4-benzyl-piperidin-1-yl)-2-bromo-ethanone (23)

Prepared as stated above for compound (22) from bromo acetic acid (935mg, 6.78 mmol) and 4-benzyl piperdine (1.02 g, 5.82 mmol) and diisopropylcarbodiimide (856 mg, 6.78 mmol) to afford compound 23, 1.53 g, (89%), (MH$^+$) m/z 297.88.

1-(4-[bis-(fluoro-phenyl)-methyl]-piperazin-1-yl)-2-bromo-ethanone (24)

Prepared as stated above for compound (22) from bromo acetic acid (551mg, 3.99 mmol) and 1-Benzhydryl-piperazine (1.0 g, 3.63 mmol) and diisopropylcarbodiimide (554 mg, 4.39 mmol) to afford compound 24, 1.10, (74%), (MH$^+$) m/z 410.88.

Library Synthesis

The bromo glycine derivites (0.25 mmol) described above (22–24) were added to the wells of a reaction block containing 5 mL of THF. To this solution was added the appropriate amine (0.5 mmol) neat. The reaction block was shaken for 24 h, filtered and concentrated. Purification was accomplished with reverse phase HPLC with H20/acetonitrile (0.1% TFA) to give the desired product as a trifluoroacetate salt. Compounds and are shown in Table 2.

TABLE 2

| # | Scheme | Product | MW | MS (m/z) | HPLC* [purity (%), RT(min)] |
|---|---|---|---|---|---|
| 1 | 3 | | 260.38 | 261.51 | >90, |
| 5 | 3 | | 350.51 | 351.21 | >90, |

TABLE 2-continued

| # | Scheme | Product | MW | MS (m/z) | HPLC* [purity (%), RT(min)] |
|---|---|---|---|---|---|
| 10 | 3 | | 362.52 | 362.51 | >90, |
| 12 | 3 | | 373.45 | 374.49 | >90, |
| 13 | 3 | | 392.59 | 393.61 | >90 |
| 10 | 3 | | 362.52 | 362.51 | >90, |
| 6 | 2 | | 350.51 | 351.2 | >95, 3.33 |
| 7 | 2 | | 350.51 | 351.2 | >95, 3.29 |

TABLE 2-continued

| # | Scheme | Product | MW | MS (m/z) | HPLC* [purity (%), RT(min)] |
|---|--------|---------|------|----------|-----------------------------|
| 8 | 2 | | 350.51 | 351.2 | >95, 3.31 |
| 15 | 2 | | 412.58 | 414.2 | >95, 3.58 |
| 16 | 2 | | 463.58 | 464.1 | >95, 3.02 |
| 17 | 2 | | 463.58 | 464.1 | >95, 3.01 |

TABLE 2-continued

| # | Scheme | Product | MW | MS (m/z) | HPLC* [purity (%), RT(min)] |
|---|---|---|---|---|---|
| 18 | 2 | (structure) | 463.58 | 464.1 | >95, 3.01 |
| 20 | 2 | (structure) | 525.65 | 526.1 | >95, 3.32 |
| 2 | 2 | (structure) | 337.47 | 338.1 | >95, 2.76 |
| 3 | 2 | (structure) | 337.47 | 338.1 | >95, 2.76 |

TABLE 2-continued

| # | Scheme | Product | MW | MS (m/z) | HPLC* [purity (%), RT(min)] |
|---|--------|---------|-----|----------|------------------------------|
| 4 | 2 | | 337.47 | 338.1 | >95, 2.78 |
| 14 | 2 | | 399.54 | 400.2 | >95, 3.20 |

*HPLC: 2.1 mm × 50 mm "Lightning" column, Jones Chromatography. 100% H20 (0.1% TFA) to 100% MeCN (0.1% TFA) over 4 min, total run time 7 min.

Synthesis Via Scheme 1

2-(Benzyl-methylamino)-1-[4-(4-fluorophenyl)-piperazin-1-yl]-propan-1-one, (9).

To a solution of N-Benzyl-N-methyl alanine (150 mg, 0.78 mmol) in 5 mL anhydrous DCM was added N,N-ethylamine (700 µL, 3.8 mmol) and pivaloyl chloride (96 µL, 0.78 mmol) drop-wise. The reaction was stirred 2 h, then treated with a solution of 4-(4-)Fluorophenyl)piperazine (177 mg, 0.699 mmol) in 2 mL anhydrous DCM drop-wise, and stirred at room temperature for 24 h. The reaction was diluted with 20 mL DCM and washed with 20 mL NaOH (1N). The aqueous layer was extracted twice with 20 mL DCM, then the combined organic fractions were washed with brine, dried over sodium sulfate, filtered, and evaporated. The residue was purified by flash chromatography (dichloromethane/methanol (0–5%)) yielding 83 mg product. To the product in diethylether (10 mL) was add HCl (g) resulting in a white precipitate. Filtration and drying in vacuum to afford 100 mg (58%) of the title compound. 1H NMR (500 MHz, CDCl$_3$): 7.50–7.25(5H, m), 7.10–6.85(4H, m), 4.0-3.52(6H, m), 3.30–2.95(4H, m) 2.35–1.80(3H, s), 1.45-1.25(4H, m). MS (MH$^+$) m/z 356.5.

2-(Benzyl-methylamino)-1-[4-(4-fluorobenzyl)-piperidin-1-yl]-propan-1-one, (11)

Title compound was prepared by the method stated above with N-Benzyl-N-methyl alanine (150 mg, 0.78 mmol,) and 4-Fluorobenzylpiperidine (161 mg, 0.699 mmol) to afford 85 mg (30% yield) as the hydrochloride salt. 1H NMR (500 MHz, CDCl$_3$) : 7.35–7.25 (5H, m), 7.10–7.05 (2H, m), 6.90–6.85 (2H, m), 4.70–4.65 (1H, m), 4.45–4.35 (1H, m) 4.10–4.05 (1H, m) 3.70–3.55 (2H, m), 2.90–2.75 (1H, m), 2.55–2.45 (2H, m) 2.15 (3H, s), 1.80–1.60 (3H, m), 1.25-1.1 (6H, m). MS (MH$^+$) m/z 369.5.

2-(Benzyl-methylamino)-1-{4-[bis-4-(4-fluorophenyl)-methyl]-piperazin-1-yl]-propan-1-one, (19)

Title compound was prepared by the method stated above with N-Benzyl-N-methyl alanine (150 mg, 0.78 mmol,) and bis-4-(4-fluorophenyl)-methylpiperazine (150 mg, 0.699 mmol) to afford 200 mg (57% yield) as the hydrochloride salt. 1H NMR (500 MHz, CDCl$_3$): 7.40–7.35 (5H, m), 7.30–7.2 (4H, m), 7.05–6.95 (4H, m), 4.21 (1H, s), 3.80-3.45 (6H, m) 2.45–2.25 (4H, m), 2.15 (3H, s), 1.30–20 (4H, m). MS (MH$^+$) m/z 464.5

EXAMPLE 3

Neuroprotection Assay

The ventral mesencephalic region was dissected out of embryonic day 15 Sprague-Dawley rat embryos (Harlan), dissociated into single cell suspension by a combination of trypsinization and trituration (Costantini et al., Neurobiol Dis., pp. 97–106 (1998). Dissociated VM cells were plated into poly-L-ornithine-coated 96-well plates at a density of 85,000 cells/well in 100 uL of DMEM supplemented with 18% heat-inactivated horse serum, 0.24% glucose, 2 mM glutamine and 50 u/ml pernicillin/streptomycin and incubated in a 5% CO$_2$ incubator. After one day in culture (DIV1), the medium was replaced with 100 µL of a defined medium (DMEM supplemented with 1×N2 cocktail (Gibco-BRL), 0.12% glucose, 2 mM glutamine, and 50 units/ml penicillin/streptomycin) containing DMSO or various concentrations of the compounds of this invention. On DIV5, neuroexcitotoxic injury was induced by the addition of various concentrations of the glutamate receptor agonist NMDA (100–400 µM). Cultures were incubated with the neurotoxin for 20 hours and the effects of neurophilin compounds were assessed using high affinity $^3$H-dopamine uptake according to a procedure published by Park and Mytilineou [Brain Res., 599, pp. 83–97 (1992)].

Table 3 below shows the results of this assay for various compounds of this invention.

TABLE 3

| Compound # | EC$_{50}$ (nM) | Compound # | EC$_{50}$ (nM) |
|---|---|---|---|
| 1 | C | 12 | C |
| 2 | C | 13 | C |
| 3 | C | 14 | C |
| 4 | C | 15 | C |
| 5 | A | 16 | C |
| 6 | B | 17 | C |
| 7 | B | 18 | C |
| 8 | B | 19 | B |
| 9 | A | 20 | C |
| 10 | B | 21 | ND |
| 11 | A | | |

In the table above, "A" designates an EC$_{50}$ of less than 100 nM; "B" designates an EC$_{50}$ of between 100 and 500 nM; and "C" designates an EC$_{50}$ of greater than 500 nM. All of the compounds tested above had EC$_{50}$ values of less than 1250 nM. It is expected that all compounds of this invention will show detectable activity in this assay.

While we have described a number of embodiments of this invention, it is apparent that our basic examples may be altered to provide other embodiments which utilize the compounds and methods of this invention. Therefore, it will be appreciated that the scope of this invention is to be defined by the appended claims rather than by the specific embodiments which have been represented by way of example.

We claim:

1. A compound having the formula (I):

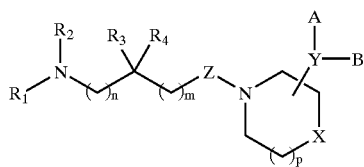

wherein:
each $R^1$, $R^2$, $R^3$ and $R^4$ are independently selected from ($C_1$–$C_{10}$)-straight or branched alkyl, Ar-substituted-($C_1$–$C_{10}$)-straight or branched alkyl, ($C_2$–$C_{10}$)-straight or branched alkenyl or alkynyl, or Ar-substituted-($C_2$–$C_{10}$)-straight or branched alkenyl or alkynyl; wherein
one to two CH$_2$ groups of said alkyl, alkenyl, or alkynyl chains in each of $R^1$, $R^2$, $R^3$ and $R^4$ are optionally and independently replaced with O, S, S(O), S(O)$_2$, C(O) or N($R^5$) in a chemically stable arrangement, wherein the CH$_2$ group of $R^1$ and $R^2$ bound directly to said nitrogen cannot be replaced with C(O); or
$R^1$ and $R^2$ taken together form a 4 to 7 membered ring; or
$R^3$ and $R^4$ taken together form a 3 to 7 membered ring; wherein a CH$_2$ in either the $R^1$ and $R^2$ ring system or the $R^3$ and $R^4$ ring system is independently and optionally replaced with O, C(O), N($R^5$), S, S(O), S(O)2 in a chemically stable arrangement; or wherein either or both of the $R^1$ and $R^2$ ring system and the $R^3$ and $R^4$ ring system is optionally fused with Ar;
Ar is selected from phenyl, 1-naphthyl, 2-naphthyl, indenyl, azulenyl, 2-furyl, 3-furyl, 2-thienyl, 3-thienyl, 2-pyridyl, 3-pyridyl, 4-pyridyl, pyrrolyl, oxazolyl, thiazolyl, imidazolyl, pyraxolyl, pyrazolinyl, pyraolidinyl, isoxazolyl, isothiazolyl, 1,2,3-oxadiazolyl, 1,2,3-triazolyl, 1,3,4-thiadiazolyl, 1,2,4-triazolyl, 1,2,4-oxadiazolyl, 1,2,4-thiadiazolyl, 1,2,3-thiadiazolyl, benoxazolyl, pyridazinyl, 2-pyrimidinyl, 4-pyrimidinyl, 5-pyrimidinyl, pyrazinyl, 1,3,5-triazinyl, 1,3,5-trithianyl, indolizinyl, indolyl, isoindolyl, 3H-indolyl, indolinyl, benzo[b]furanyl, benzo[b]thiophenyl, 1H-indazolyl, benzimidazolyl, benzthiazolyl, purinyl, 4H-quinolizinyl, quinolinyl, 1,2,3,4-tetrahydroisoquinolinyl, isoquinolinyl, 1,2,3,4-tetrahydroquinolinyl, cinnolinyl, phthalazinyl, quinazolinyl, quinoxalinyl, 1,8-naphthyridinyl, or any other chemically stable monocyclic or bicyclic ring system, wherein each ring consists of 5 to 7 ring atoms and wherein each ring comprises 0 to 3 heteroatoms independently selected from N, O, or S in a chemically stable arrangement, wherein
each Ar is optionally and independently substituted with one to three substituents selected from halo, hydroxy, nitro, =O, —SO$_3$H, trifluoromethyl, trifluoromethoxy, ($C_1$–$C_6$)-straight or branched alkyl, ($C_1$–$C_6$)-straight or branched alkenyl, O—[($C_1$–$C_6$)-straight or branched alkyl], O—[($C_1$–$C_6$)-straight or branched alkenyl], O-benzyl, O-phenyl, 1,2-methylenedioxy, —N($R^6$)($R^7$), carboxyl, N-($C_1$–$C_6$-straight or branched alkyl or $C_2$–$C_6$-straight or branched alkenyl) carboxamides, N,N-di-($C_1$–$C_6$-straight or branched alkyl or $C_2$–$C_6$-straight or branched alkenyl) carboxamides, N-($C_1$–$C_6$-straight or branched alkyl or $C_2$–$C_6$-straight or branched alkenyl) sulfonamides, or N,N-di-($C_1$–$C_6$-straight or branched alkyl or C2–C6-straight or branched alkenyl) sulfonamides;
each of $R^6$ and $R^7$ are independently selected from ($C_1$–$C_6$)-straight or branched alkyl, ($C_2$–$C_6$)-straight or branched alkenyl or alkynyl, hydrogen, phenyl or benzyl; or wherein $R^6$ and $R^7$ are taken together with the nitrogen atom to which they are bound to form a 5–7 membered heterocyclic ring;
each $R^5$ is independently selected from hydrogen, ($C_1$–$C_6$)-straight or branched alkyl, or ($C_2$–$C_6$)-straight or branched alkenyl or alkynyl, Ar, Ar-substituted ($C_1$–$C_6$)-straight or branched alkyl, or ($C_2$–$C_6$)-straight or branched alkenyl or alkynyl or Ar-disubstituted ($C_1$–$C_6$)-straight or branched alkyl, or ($C_2$–$C_6$)-straight or branched alkenyl or alkynyl;
n is 0 or 1 and m is 0 or 1;
X is selected from C($R^5$)$_2$;
Y is a bond;
Z is —C(O)—;
p is 1;
A is hydrogen;
B is absent.

2. The compound according to claim 1, wherein Ar is selected from phenyl, 1-naphthyl, 2-naphthyl, indanyl, azulenyl, 2-furyl, 3-furyl, 2-thienyl, 3-thienyl, 2-pyridyl, 3-pyridyl, 4-pyridyl, pyrrolyl, imidazolyl, benzo[b]furanyl, benzimidazolyl, quinolinyl or isoquinolinyl.

3. The compound according to claim 2, Ar is selected from phenyl, indanyl, 2-pyridyl, 3-pyridyl, 4-pyridyl, imidazolyl, benzo[b]furanyl, 2-benzimidazolyl, quinolinyl or isoquinolinyl.

4. The compound according to claim 1, wherein each of $R^1$ or $R^2$ is independently selected from ($C_1$–$C_6$)-straight alkyl, or ($C_1$–$C_6$)-straight alkyl-Ar.

5. The compound according to claim 4, wherein $R^1$ is selected from methyl, ethyl, benzyl, chlorobenzyl, dichlorobenzyl, bromobenzyl, fluorobenzyl, or methoxybenzyl.

6. The compound according to claim 5, wherein $R^1$ is selected from methyl, ethyl, 3-methyl-but-2-enyl, benzyl, 3-methoxybenzyl, or 3-fluorobenzyl.

7. The compound according to claim 1, wherein said compound is as shown in Table 1 below.

TABLE 1

| # | Structure |
|---|-----------|
| 10 | 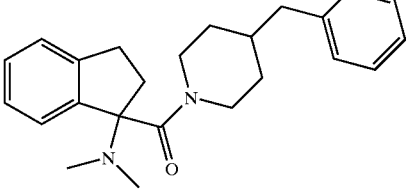 |

* * * * *